United States Patent
Weinert et al.

(10) Patent No.: US 10,321,972 B2
(45) Date of Patent: Jun. 18, 2019

(54) DEVICE AND METHOD FOR SIMULTANEOUSLY IDENTIFYING A PLURALITY OF SURGICAL INSTRUMENTS

(71) Applicant: Aesculap AG, Tuttlingen (DE)

(72) Inventors: Markus Weinert, Wurmlingen (DE); Nicola Giordano, Villingen-Schwenningen (DE); Pedro Morales, Tuttlingen (DE); Dieter Weisshaupt, Immendingen (DE)

(73) Assignee: Aesculap AG (DE)

( * ) Notice: Subject to any disclaimer, the term of this patent is extended or adjusted under 35 U.S.C. 154(b) by 0 days.

(21) Appl. No.: 15/906,636

(22) Filed: Feb. 27, 2018

(65) Prior Publication Data

US 2018/0214243 A1 Aug. 2, 2018

Related U.S. Application Data

(63) Continuation of application No. 14/417,384, filed as application No. PCT/EP2013/066306 on Aug. 2, 2013, now Pat. No. 9,937,010.

(30) Foreign Application Priority Data

Aug. 8, 2012 (DE) .......................... 10 2012 107 274

(51) Int. Cl.
*A61B 90/90* (2016.01)
*G06K 7/10* (2006.01)
(Continued)

(52) U.S. Cl.
CPC .............. *A61B 90/90* (2016.02); *A61B 90/98* (2016.02); *G06K 7/10366* (2013.01); *G06K 9/00624* (2013.01)

(58) Field of Classification Search
None
See application file for complete search history.

(56) References Cited

U.S. PATENT DOCUMENTS 7,118,029 B2 10/2006 Nyez et al.
2004/0118920 A1 6/2004 He
(Continued)

FOREIGN PATENT DOCUMENTS

DE 4241663 A1 6/1994
DE 19806822 A1 8/1999
(Continued)

OTHER PUBLICATIONS

Chinese Office Action for Chinese Application No. 201380041956. X, dated Jul. 5, 2016—6 pages.
(Continued)

*Primary Examiner* — Leon Viet Q Nguyen
(74) *Attorney, Agent, or Firm* — RatnerPrestia

(57) ABSTRACT

A device for simultaneously identifying a plurality of surgical instruments or instrument groups includes a first detecting device having a first detection technology for detecting instruments and, if applicable, related instrument-specific information. The device also includes a second detecting device having a second different detection technology for detecting instruments and instrument information. Moreover, the device includes a comparing device for comparing the detection results of the two detecting devices. The comparing device outputs a positive evaluation regarding the correctness of the detected instruments if the two detection results are matching.

5 Claims, 2 Drawing Sheets

(51) Int. Cl.
*G06K 9/00* (2006.01)
*A61B 90/98* (2016.01)

(56) References Cited

U.S. PATENT DOCUMENTS

| | | |
|---|---|---|
| 2004/0186683 A1 | 9/2004 | Farber et al. |
| 2006/0043177 A1* | 3/2006 | Nycz .................... G06Q 10/087 235/385 |
| 2007/0210159 A1 | 9/2007 | Mott et al. |
| 2011/0036738 A1 | 2/2011 | Hiltl |
| 2011/0156869 A1* | 6/2011 | Watt .................... G06K 7/0004 340/10.1 |
| 2013/0091679 A1 | 4/2013 | Gloger et al. |

FOREIGN PATENT DOCUMENTS

| | | |
|---|---|---|
| DE | 69813533 T2 | 2/2004 |
| DE | 69830085 T2 | 1/2006 |
| DE | 102005047522 A1 | 4/2007 |
| DE | 102008008231 A1 | 8/2009 |
| DE | 102009037315 A1 | 2/2011 |
| EP | 2287091 A1 | 2/2011 |
| EP | 2581863 A1 | 4/2013 |
| JP | 2003111772 A | 4/2003 |
| JP | 2008144409 A | 6/2008 |
| JP | 2009291308 A | 12/2009 |
| JP | 3173997 U | 3/2012 |
| WO | 2006086603 A2 | 8/2006 |

OTHER PUBLICATIONS

European Exam Report for European Application No. 13 745 076.3, dated Sep. 21, 2015—10 pages.
Extended European Search Report for European Application No. 1619557.8, dated Jan. 24, 2017—14 pages.
German Search Report for German Application No. 10 2012 107 274.4, dated Feb. 13, 2013—6 pages.
International Search Report and Written Opinion for International Application No. PCT/EP2013/066306, dated Nov. 11, 2013—8 pages.
Japanese Office Action for Japanese Application No. 2015-525840, dated Apr. 20, 2017—4 pages.
Entire patent prosecution history of U.S. Appl. No. 14/417,384, filed Jan. 26, 2015, entitled "Device and Method for Simultaneously Identifying a Plurality of Surgical Instruments," now U.S. Pat. No. 9,937,010, dated Apr. 10, 2018.
European Communication for European Application No. 16 195 577.8, dated Sep. 3, 2018, with translation, 11 pages.

* cited by examiner ration
DEVICE AND METHOD FOR SIMULTANEOUSLY IDENTIFYING A PLURALITY OF SURGICAL INSTRUMENTS

RELATED APPLICATIONS

This application is a continuation of U.S. application Ser. No. 14/417,384, filed Jan. 26, 2015, which is the United States National Phase entry of International Application No. PCT/EP2013/066306, filed Aug. 2, 2013, which claims the benefit of priority of German Application No. 10 2012 107 274.4, filed Aug. 8, 2012. The contents of U.S. application Ser. No. 14/417,384, International Application No. PCT/EP2013/066306, and German Application No. 10 2012 107 274.4 are incorporated by reference herein in their entireties.

FIELD

The invention relates to a device and method for simultaneously identifying a plurality of different surgical instruments or instrument groups.

BACKGROUND

In the public health sector, there is an increasingly clear trend toward single instrument tracking in order to be able to track the respective medical products to the field of instruments and sterile goods so as to be able to establish and track the frequency of use, the service intervals or the current storage place. For example, completeness checks of basket contents at the most different stations of an instrument circulation serve for ensuring sterile goods to be utilized completely and in the correct configuration.

Furthermore they serve for reducing the great and cost-intensive loss of instruments.

They further serve for patient safety to a particular extent. This aspect gains importance against the background that in the case of emergency operation sometimes about 100 pressing rolls and 40 pads are used apart from the other instruments. It is moreover known from hospital statistics that on average 3000 cases occur each year in which foreign matters such as cloths, swabs or the like remain in patients' bodies after surgical interventions.

Apart from traditional manual techniques such as sorting and counting in the meantime most various technologies have been employed to assist or even fully automatically run the detection of surgical instruments. These include, for instance, radio identification by means of RFID (radio frequency identification) technology, weight measurement, optical identification, barcode detection etc.

Previous solutions are frequently based on individually reading out instruments or the sterile goods, respectively, which is time-intensive. Therefore the individual manual detection of individual instruments was developed into the automated individual instrument detection. Accordingly, mainly the reduction of the processing times is in the fore so as to save time and costs. Equally high processing safety is absolutely necessary so as to facilitate automation for simultaneously saving time and costs. It is a drawback of the individual instrument detection that the reading process is very time-consuming in the case of a plurality of objects and instruments, respectively.

A further known solution therefore is to simultaneously detect a plurality of instruments to reduce the processing times in this way especially in contrast to individual readings in instrument tracking (e.g. with Data Matrix). As suggested by U.S. Pat. No. 7,118,029 B2, plural instruments marked with RFID tags (RFID instruments) lying in a basket are simultaneously detected, are compared to basket lists and possibly incorrectly sorted instruments are identified.

Since the RFID transponder at the surgical instrument cannot be configured to have any size, usually passive RFID tags which are operated by the high-frequency electromagnetic alternating field generated by the RFID reader have to be used. As the field of radiation decreases quadratically with the distance, a rather high transmission power must be applied. Especially in the medical environment this is possible to a restricted extent only so as to avoid possible interferences with other highly sensitive devices, in particular in the operating room.

In the case of this so called batch detection overlapping and covered instruments in the basket or container may entail the fact that some of the instruments to be detected are detected incorrectly or not at all by the reader used and are thus missed. Furthermore, the related poor probability of identification as well as the lower processing reliability results in the fact that the reading operation cannot be automated. As a consequence, also with this solution increased processing times and costs have to be accepted.

Since by the already known systems either high processing reliability is realized at the expense of the processing speed or a high processing speed is realized at the expense of the processing reliability and thus of automation, there is a need for action in further developing the reading systems.

Against this background, the object underlying the invention is to provide a device and a method adapted to reliably detect a plurality of different instruments simultaneously and with high identification probability.

This object is achieved by the features described herein.

SUMMARY

In the device according to the invention a combination of a first detection means having a first detecting technology for detecting instruments and instrument information, especially RFID identification, and a second detection means having a second detecting technology different from the first one for detecting instruments and instrument information as well as a comparing device for comparing the detection results of the two detection technologies is used. If the compared detection results are matching, the comparing device outputs a positive evaluation regarding the correctness of the detected instruments and, resp., verifies the detection results so that accordingly further steps can be taken, e.g. that the detected instruments are registered or that an operating person is informed about the fact that all instruments have been correctly detected.

Thus the device allows the batch detection of a plurality of different instruments and sterile goods, respectively. It offers the advantage that in logistic processes such as, for example, in automatic instrument identification the instruments lying in a basket or container are detected simultaneously or in one reading operation without any separation which incurs costs.

Furthermore, by the rapid batch detection at the most different positions in the instrument circulation or process of the instruments, process information which has not been available so far, such as dwell times ahead of and/or behind the respective process stations, is obtained without any major time expenditure. With the aid of this evaluable information both the process reliability and the process cycle can be improved.

Moreover it is ensured by the use of at least two different detection technologies that all instruments to be detected are detected and possible not detectable areas or instruments of the one technology are detected by the other technology or that at least the identification probability and thus the process reliability can be substantially increased. In addition, instruments which are not identifiable to the first detection technology in general, e.g. when the RFID tag or barcode is lost, or due to the current differences are detected by the second detection technology.

Hence especially the advantages of the different detection technologies are exploited by the combination of the advantages of the respective technology. In this way combined apparatuses having plural integrated instrument detecting systems are provided with the objective to maximize the probability of identification of basket contents. Thus the redundant detection of the instruments by two different detection technologies for the first time enables a detection result to be identified as a wrong result and to be notified to the operating person.

Moreover the reading operations required until a correct detection result is provided are reduced so that by the reduction of the error output the processing rates can be increased, whereby the process times are definitely reduced. This in turn permits automating the instrument identification.

In the field of medical engineering, especially in surgery, comparatively strict requirements are prevailing for the operating room. Since, as already mentioned in the beginning, sensitive technical apparatuses are used here, they must by no means be disturbed by the radio power of the RFID device. Due to the reduction of the reading energy also the probability of identification of this detection technology is reduced. Therefore, exactly in such case it is of particular advantage that the RFID technology is supported by a thither technology which does not or less influence the apparatuses present in the operating room.

It is of advantage in the present invention that the detection results of the two technologies are compared by the comparing device. This ensures that all instruments to be detected are correctly detected and identified and a faulty detection result is identified. When a deviation between the two results is determined, further measures such as a repeated reading operation, a variation of the quantity or position of the instruments to be detected can be initiated.

Each detection technology possibly detects more or less information about a particular detected instrument. After verification of the detection results the detection result of the detecting device which provides most information about the instruments detected can be further used or processed. However, in this way also the information detected by a detecting device about a particular instrument can be supplemented, if applicable, by the information established by the other detecting device.

By the use of two different technologies and the comparison of the two detection results to each other the device according to the invention thus can work in a self-sustained way, i.e. without any comparisons to predetermined lists of content, as it carries out a plausibility test so to speak on its own.

Nevertheless, in a further development the comparing device can compare the two detection results to a predetermined data set, especially an instrument or basket list in which the entire basket content is listed, wherein the comparing device can output a positive evaluation, if at least one of the two detection results is matching the predetermined data set.

The predetermined data set can be an externally generated list input in the device or instrument list resp., containing the individual instruments of predetermined instrument configurations or sets. Equally the list can be a list generated internally in the device which was generated based on preceding reading operations and was intermediately stored.

This is important especially for completeness checks before, during and after packing operations of baskets.

Especially in instrument management systems completeness checks are of particular importance, as they have to be constantly maintained and updated.

When at least one of the detecting devices has identified all instruments listed on the instrument list, it can be assumed that the detection of this device is correct. When, consequently, after comparing the first and second detection result to the deposited data set it is determined that at least one detection result has detected all instruments listed on the list, all further reading operation, are thus dropped, which in turn results in further time saving.

Furthermore, in the case of multiple identification the data list comparison offers the advantage that completeness checks can be carried out when basket and loan baskets are compiled. Equally completeness checks can be carried out for baskets having a particular customized configuration.

Especially the counter-check with deposited lists is advantageous to the effect that undesired loss of partly cost-intensive instruments and/or sterile goods is minimized. This is achieved in that the instruments are detected prior to and after each kind of use and/or washing operation and the like.

Of particular advantage is the increased patient's safety by completeness checks of the used instruments prior to and after operation. In this way, on the one hand used and still missing instruments are identified. Furthermore it is likewise determined in this way that there are still instruments provided which should have been used, if applicable. This aspect is of major importance especially against the background that operations must not be concluded before all instruments used are complete and that each minute of operation is expensive, especially when a lot of instruments are used.

In a further development the device for simultaneous identification of instruments can be configured so that the comparing device outputs a positive evaluation, if at least one combination of the detection results is matching a predetermined data set.

This is especially advantageous when some of the instruments to be detected cannot be detected by the one detection technology due to unfavorable positioning, for example, while other instruments in turn cannot be detected by the other detection technology. By this further development all detected instruments are compared to a respective data set. If then the respective instruments detected by the two detection technologies correspond to the predetermined data set at least in synopsis, the comparing device output a positive evaluation.

It is especially preferred that the device may include a vibrating means and/or a conveyor belt means for separating the instruments upstream or downstream in time and/or in place as well as a control device for controlling the vibrating and/or conveyor belt means. The latter operates the vibrating and/or conveyor belt means at least once for a predetermined period of time and before the instrument information is repeatedly detected and compared by the comparing device.

Before reading of the instruments starts, the vibrating and or conveyor belt means thus can be operated until the instruments to be detected are largely distributed in the basket. This period of time can be either predetermined or monitored by the operator. During and, resp., after a reading operation the device can equally be operated to vary the current instrument order, for example.

Usually a repeated reading operation follows a vibrating operation, wherein this cycle can be repeated as often as required, preferably for several times in order to finally detect all instruments.

It is advantageous that mutual overlapping and/or covered instruments as well as unfavorable positions of the instruments to be detected are eliminated. This entails the advantage that higher identification probability and thus process reliability are achieved. Furthermore, an even better automation of the reading operation of a multiple identification of a plurality of instruments is obtained in that the means for identifying instruments in the case of negative evaluation includes its own remedy measure, namely operating the vibrating and/or conveyor belt means for spacing the instruments apart from each other.

In a further development the invention may include a display device by which evaluations about the completeness and the correctness of the detection results as well as the detected instruments are displayed. Furthermore, in the case of incomplete detection it can be displayed and emphasized, respectively, which instruments of the current instrument list were not yet detected. Accordingly, the operator can specifically search for these instruments where necessary, add them manually and in this way successfully complete the reading operation.

By the display moreover product-specific additional information obtained in the data set such as a specific treatment and/or handling of selected instruments can be displayed. Moreover, the additional information may consist in the fact that particular further instruments have to be added to a detected instrument or a component thereof, such as e.g. wear part, has to be exchanged.

Advantageously, it is directly displayed on the display device that an inspection is pending, the instrument is a loan or an instrument has to be disposed of, for example.

When the detected instruments are instruments to be purified which come from an operating room and when dismounting is, required for this purpose, moreover helpful information such as dismounting instructions or pictures are displayed. When by way of exception a specific washing program or a cleaning additive has to be added, the, operator is also accordingly informed.

It turns out to be especially advantageous when the device is further provided with means for varying a relative orientation and/or a relative distance between the instruments and the detecting devices.

Advantageously in an event when a positive evaluation cannot yet be output, both orientation and distance between the instruments and the detecting devices can be varied by moving at least one detecting means and/or the instruments so as to increase the probability of complete read-out. For this purpose, a detecting device is movable relative to the instrument base or container and vice versa.

Consequently also instalments being further distanced from the detecting device or being covered, resp., are detected without the reading power having to be increased. This is of advantage especially when the reading power is intended to have as little impact on the environment as possible. In this way the instruments are completely detected without the housing in which the detecting device is installed having to be shielded or shielded more strongly.

In order to be able to subject the detection results to plausibility check the device of the present invention further may include scales for weight detection. The comparing device carries out a plausibility check of the evaluation in dependence on the identified instruments and their weight data deposited in the data set by comparing a detected actual weight to a deposited set weight. Based on the plausibility check it outputs a negative evaluation, if the actual weight does not match the set weight, and it outputs a positive evaluation, if the actual weight matches the set weight.

Automation can be better realized by weight detection, as error outputs are reduced by a further check of the detection results.

In an especially preferred further development the device can be configured as a so-called tunnel reader having a shielded or shieldable housing in which or within which at least two, preferably all different detecting devices are arranged and form an integrated unit. In this way the instruments to be detected can be detected all at once by the tunnel reader. Furthermore the tunnel reader can be completely shielded from the environment during the reading operation by closing one or more flaps in order not to impair an external area, especially the operating area. This offers the advantage that the reading powers can be higher and consequently the identification probability is improved.

A slide-in case can be operable both manually and automatically by a flap.

Alternatively, the tunnel reader can be configured in the form of a pass-through having an open back wall especially in the operating area. In this way the sterile goods is directly detected and passed into the operating area. The instruments used in the operating area then can be returned on the same way. This further development offers the advantage that immediately after use of the instruments a completeness check is carried out, whereby the patients' safety is definitely improved. This is especially advantageous as during operation no additional staff members are required who have to deal with counting the instruments.

The tunnel reader can be designed especially advantageously when the pass-through has a lockable flap only on one side, preferably on the side of the operating area, so that an inserting case can be closed after introducing the basket to be read. The interior of the tunnel reader then can be shielded, prior to the reading operation, substantially completely from the operating area so that the latter is not impaired even in the case of higher wattages of the RFID identification.

Thus it is especially advantageous hen the tunnel reader is applied in the course of an operation, especially against the background of the patient's safety. The application is not restricted hereto, however, but can equally be preferably used prior to and after a transport of instruments, a cleaning/disinfecting operation or sterilizing operation. This applies equally to packing operations and removals for the repair of individual instruments.

In a method according to the invention for simultaneously identifying a plurality of, preferably different surgical instruments or instrument groups, initially the respective instruments are detected by first and second detecting devices and first and second detection results are output which are then compared to each other by a comparing device, wherein a positive evaluation of this comparison is output if the two detecting results are matching.

The detection results are advantageously compared to a first instrument list in a further step. If at least one of the detection results is matching the instrument list a positive evaluation is output.

Thus a positive evaluation can also be determined if at least one of the detection results is matching the instrument list.

The method step in which a combination of the detection results is compared to the predetermined instrument list is of special advantage. This comparison entails a positive determination if at least one combination of the detection results is matching the instrument list.

As a consequence, a positive evaluation can be determined if none of the detection results but at least a combination of the same is matching the instrument list.

The afore-mentioned method turns out to be especially advantageous in combination with a vibrating do rise which can be operated for as predetermined period of time. This step is important in particular when in a first detecting step no positive evaluation was determined. Following the actuation of the vibrating device the detection results are repeatedly detected.

As required, the duration, the type and repetitions of the actuation of the vibrating device can be automatically controlled according to a predetermined pattern or by an operating person. In this way an adaptation to the content of the basket is possible.

Hence the method equally realizes the advantages listed in the beginning in connection with the device according to the invention.

BRIEF DESCRIPTION OF THE DRAWINGS

Hereinafter an embodiment of a device according to the invention for simultaneously identifying a plurality of different surgical instruments will be illustrated with reference to the enclosed drawings, in which.

DETAILED DESCRIPTION

Figure 1:
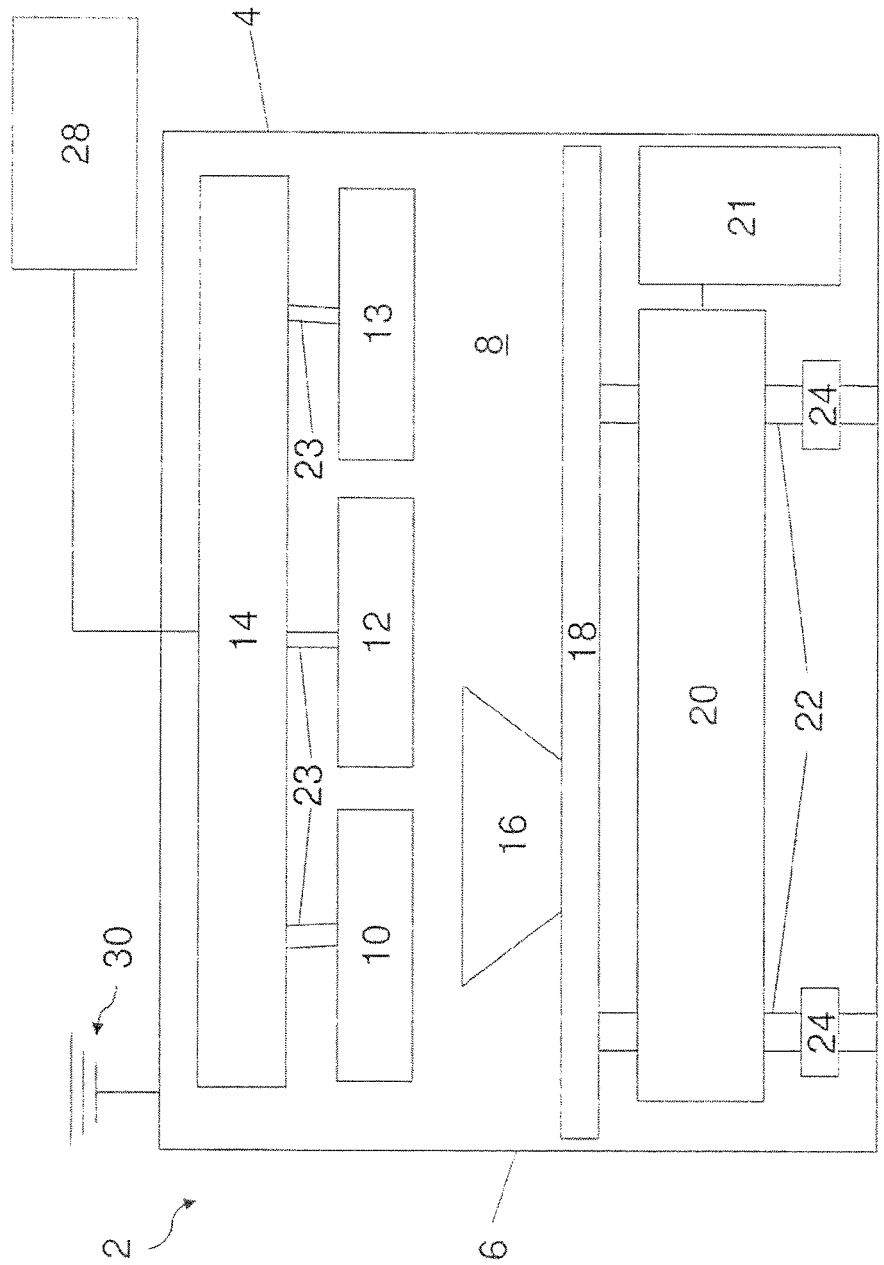
FIG. 1 shows a schematic sectional view of a tunnel reader of the present invention in a side view.

FIG. 1 exemplifies in a side view a tunnel reader 2 for simultaneously identifying a plurality of preferably different surgical instruments. The housing 4 thereof substantially takes the shape of a cuboid including in the longitudinal direction of the tunnel reader 2 at each of its two side faces an aperture 6 forming the two ends of a passage 8 longitudinally extending through the housing 4 and having a preferably rectangular cross-section. The apertures 6 can be closed by respective flaps (not shown).

The to reader 2 includes an RFID reader 10 as a first detecting device, an optical reader or camera 12 as second detecting device, a barcode scanner 13 as third detecting device and a scale 24 as fourth detecting device, all of which are cross-linked with a comparing device 14 and are in data exchange. The devices 10, 12, 13, 14, 24 are arranged inside the housing 4. The first to third detecting devices 10, 12, 13 are arranged at an upper portion of the passage 8 so that they face a receptacle or basket 16 introduced into the tunnel reader 2, while the scale 24 for weight measurement is provided beneath the basket 16.

The passage 8 includes a bottom for supporting the basket 16, said bottom being preferably configured as a conveyor belt 18. The conveyor belt 18 is connected to the housing 4 not directly but via a vibrating means 20, wherein the vibrating means 20 is preferably mounted beneath the conveyor belt 18 or at the side portions thereof, is coupled to the same and further connected to the housing 4 so as to vibrate the latter. Furthermore, the vibrating means 20 includes a control device 21 for controlling the vibrating means 20 and the conveyor belt 18 which communicates with the comparing device 14. In response to an evaluation of the comparing device 14, the control device 21 controls the conveyor belt 18 and/or the vibrating means 20. In this way both the orientation of the instruments in the basket 16 and the position of the entire basket 16 relative to the detecting devices 10, 12, 13 can be varied. In addition, the conveyor belt 18 can vibrate the basket 16 by short and quickly successive changes in direction of the conveyor belt 18.

Moreover the detecting devices 10, 12, 13 are mounted via respective telescopic holding fixtures 23 including an electric motor (not shown) on the housing 4 so that they can be lowered individually or jointly in order to reduce the distance from the basket 16. This operation is controlled by the control device 21 based on a signal from the comparing device 14.

The vibrating means 20 is supported on the housing 4 via columns 22, wherein measuring, elements (scale) 24 for weight measurement are integrated in the columns 22 so as to be able to detect the weight weighing on the conveyor belt 18.

So that the comparing device 14 is adapted to display evaluations it is electronically connected to a display device 28 provide at the tunnel reader 2. The display device is provided at a position clearly visible to an operating person. It is preferably mounted on the tunnel reader 2, but it can equally be part of a separate and data-communicated operating means. In this case the information can be transmitted wirelessly to the equally wireless comparing device 14 via an antenna device 30.

Depending on the place of use the tunnel reader 2 can be placed on posts or a support (not shown).

The tunnel reader 2 can also be a lock mounted in a partition wall. Such pass-through system having an open back wall, where applicable, is of advantage e specially in the operating area to transfer the scanned sterile goods into the sterile operating area, where it serves as an interface between the pure sterile area and the impure unsterile area.

Figure 2:
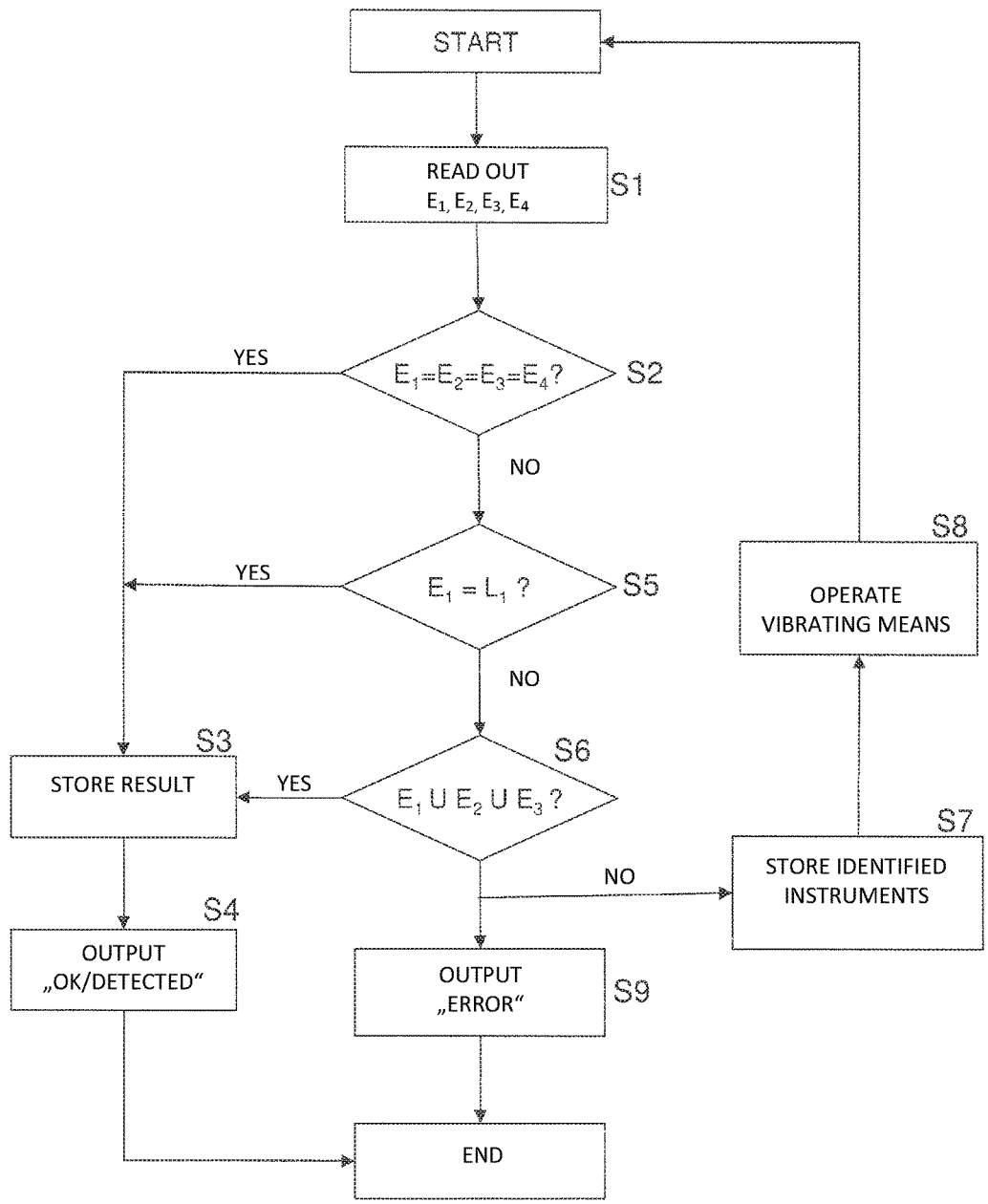
FIG. 2 shows a flow chart for illustrating simultaneous identification of a plurality of surgical instruments or instrument groups.

FIG. 2 exemplifies a flow chart for illustrating a flow of the tunnel reader 2 for simultaneously identifying a plurality of surgical instruments or instrument groups.

Hereinafter a detecting process is described in detail making use of the flow chart shown in FIG. 2, when an identifying control for simultaneously identifying a plurality of surgical instruments is performed.

After the start of the automatic instrument identification in step S1 the instruments provided in the passage 8 of the tunnel reader 2 are detected by the detecting devices 10, 12, 13, 24 simultaneously and directly successively and the four detection results $E_1$ to $E_4$ are read out. The first detecting device, i.e. the RFID reader 10, detects the first detection result $E_1$, wherein the respective instrument is unambiguously identified by radio transmission of information. The RFID reader 10 turns out to be a relatively reliable technology for instrument detection, as it requires no free view onto the instruments and the instruments neither have to be exposed nor have to face the reader. Moreover, on the RFID transponder a plurality of information such as instrument designation and part number as well as information about the manufacturer, maintenance and repair work carried out, frequency of use etc. may be deposited which cannot be detected by a mere identification of shape.

The RFID reader 10 of the present invention can work in different frequency ranges. Depending on the requirements of reading rate, range and the like, the selection falls on the corresponding frequency range. Preferably, the RFID reader 10 operates in the LF range (low frequency) at approx. 125 kHz, in the HF range (high frequency) at approx. 13.56 MHz, in the range (ultrahigh frequency) at approx. 870 MHz or in SAW (surface acoustic wave) technology.

The second detecting device, i.e. the optical identifying device or camera 12, detects images of the instruments which are assigned to a type of instrument and thus to the detection result $E_2$ by comparison with deposited images based on the shape, size and proportions thereof. Accordingly, although the second detecting device identifies the type of instruments such as scissors, scalpel or the like and the number thereof with the aid of the images taken by the camera 12, it is not capable of unambiguously identifying them, however. It has to be noted in this context that the instruments to be detected should preferably be exposed so as to be identified. This can preferably be achieved by the vibrating means 20. When, however, so many instruments are placed in a basket 16 that a substantially complete separation of all instruments to be detected is not possible, they can be separately put onto the conveyor belt 18 and detected by the camera 12.

The barcode scanner 13 detects, as the third detecting device, the detection result $E_3$ which equally permits unambiguous identification and the detection of additional instrument-specific information. In this context, it has to be noted that the barcode must be visible to the barcode scanner 13. The barcode reader may be suited for reading one-dimensional and/or two-dimensional codes (Data Matrix).

The scale 24 as the fourth detecting device detects the weight of the instruments to be, detected as detection result $E_4$. The weight can be detected most easily, by way of comparison has the least information content and preferably serves as lower-ranking plausibility check vis-à-vis the other detection results $E_1$ to $E_3$.

A detection result of the detection technologies can represent a number of detected instruments so that completeness in terms of quantity can be checked and confirmed. It can equally represent lists of the types of instruments and the respective number thereof (such as three cloths, two clips and the like) so that the presence of a required object in the correct quantity can be checked. This is the case especially with the camera 12.

Likewise a detection result may be a list of exactly identified instruments, which is facilitated by the radio and barcode system.

In step S2 the comparing device 14 determines whether the detection results $E_1$ to $E_4$ are matching. If the comparing device 14 determines in step S2 that $E_1$ to $E_4$ are matching ("YES" in step S2), the control device 21 passes on to step S3. Accordingly, the same instruments were detected by each of the three detecting devices 10, 12 and 13. Furthermore, the detected total weight $E_4$ thereof matches the deposited data. In this case the control device 21 assumes that all instruments to be detected were correctly detected and in step S3 stores the result of detection which contains all identified instruments.

Then the control device 21 in step S4 orders an output "RESULT IN ORDER AND DETECTED" on the display device 28 and the cycle is completed. Instead of a text display also a particular symbol or merely a green light can be displayed.

If, however, in step S2 a negative evaluation is determined ("NO" in step 2), the control device 21 passes on to step S5. Here it is determined whether the detection result $E_1$ matches a predetermined data set or instrument list $L_1$ deposited in the comparing device 14. If it is determined in step S5 that $E_1$ is matching $L_1$ ("YES" in step S5), the control device 21 passes on to the steps S3 and S4, as described above, and the cycle is completed. In this case the most telling and most reliable $E_1$ is prioritized over the other technologies by the control device 21.

If, however, in step S5 a negative evaluation is determined ("NO" in step S5), the control device 21 passes on to step S6.

In step S6 the comparing device 14 determines whether $E_1$ in combination with the other results $E_2$ and $E_3$ contains the content of the list $L_1$. If a few instruments of the list $L_1$ were not detected by the RFID reader 10, the two other results are resorted to in order to still achieve a positive result.

If in step S6 a positive evaluation is determined ("YES" in step S6), the control device 21 passes on to the steps S3 and S4 as described above and the cycle is completed.

If, however, in, step S6 a negative evaluation is determined ("NO" in step S6), the control device 21 passes on to step S7 in which the currently identified instruments are stored as an intermediate result. In the following step 8 the vibrating means 20 is actuated by the control device 21 for a predetermined period of time in order to change the current order of the instruments present in the basket 16. In this way especially covered instruments which thus are not visible to the camera 12 and the barcode reader 13 are to be exposed.

Then the control device 21 passes on to step S1 and the already afore-described cycle follows to the step S1. However, it has to be assumed that the instruments not detected during the first reading operation of the RFID reader might continue not to be detected due to malfunction of the RFID tag so that the redundant systems are resorted to. When after step S2 four matching detection, results $E_1$ to $E_4$ or otherwise after step S5 coincidence of the newly detected $E_1$ with $L_1$ are provided, the cycle passes on to the steps S3 and S4, as afore-described, and the cycle is completed.

If the determination in both steps S2 and S5 is negative, the cycle passes on to step S6. In this step the comparing device 14 determines, as afore-described, whether a combination of the detection results $E_1$ to $E_3$ contains of the content of the list $L_1$. Unless this is the case again, the comparing device 14 compares in a synopsis of all detection results whether all instruments listed on the list $L_1$ could be identified. Since the instruments are unambiguously identified by means of radio technology and the barcode scanner, even upon comparing the detection results of plural reading operations the same instrument is not counted twice.

Depending on the number of cycles of the steps S7 and S8, a different number of detection results are provided. It can be stored in advance or controlled by the operating person how often a repeated attempt of complete detection is run.

Deviating from the afore-shown embodiment, the tunnel reader 2 may vary both by its length and by its height so that baskets 16 of different sizes and a plurality of baskets 16 can be accommodated all at once by the tunnel reader 2 as long as it is ensured that the detected instruments can be assigned to a particular basket 16.

At the display device 28 both the evaluations of the comparing device 14 and further pieces of information such as indications of required special purifying programs, indications of required preparation measures (dismounting, pretreatment), inspection instructions as well as instructions to exchange/dispose of individual instruments can be displayed. This information can be transmitted to the display device 28 including a receiver unit (not shown) for example via an antenna 30 arranged at the tunnel reader 2.

The scale 24 for weight measurement of the objects to be detected can also be arranged at the lower housing side, in the posts 30 or the like.

The vibrating means 20 can also be arranged at an area ahead of or behind the housing 4 so that the instruments to be detected are accordingly vibrated ahead of or behind the tunnel reader 2. By arranging the vibrating means 20 outside the housing the operating person can observe and control the vibration process.

Instead of a telescopic device 23 driven by an electric motor, the detecting devices can also be lowered via a cable pull in the direction of the basket 16 and can be varied as to their orientation, where necessary. Equally each of the detecting devices can be arranged on a rail extending perpendicularly to the longitudinal direction of the tunnel reader 2, the rail being bent from its center in the longitudinal direction downwards in the direction of the two ends.

Furthermore, each of the detecting devices may include a separate reading unit so that only the latter is movable and can vary a reading distance from the instruments.

Hence the invention discloses a device and a method suited for multiple readability of complete instrument baskets. This is achieved especially by a combination of different identification systems which are cross-linked and communicate with each other in a device. The respective detection results are compared to each other as well as to predetermined instrument lists. The device thus detects instrument information via a radio identification system and an additional optical identification system and/or a barcode scanner, wherein a scale checks the detection results by plausibility check. In support thereof a vibrating system and/or a conveyor belt system are used which can be operated in most different ways such as a continuous and/or intermittent manner. Thus combined devices including plural integrated instrument detection systems are provided with the objective to maximize the probability of identification of basket contents. Due to an approximately hundred percent detection safety, time and costs are saved by automating the reading operation and the safety during handling of surgical instruments is increased.

Despite a metallic environment due to instruments, the basket and containers, the device is suited for completely detecting disordered and partly or completely overlapping instruments in the basket independently of the number and the position of the respective instruments.

What is claimed:

1. A device for simultaneously identifying a plurality of different surgical instruments or instrument groups, comprising:
   a first detecting device including a first detection technology for detecting instruments and possibly related instrument-specific information as a first detection result;
   a second detecting device including a second detection technology different from the first detection technology, the second detection technology for detecting instruments and possibly related instrument-specific information as a second detection result;
   a conveyor belt device for moving the plurality of different surgical instruments or instrument groups relative to the first and second detecting devices;
   a vibrating device for separating the plurality of different surgical instruments or instrument groups arranged upstream or downstream in time and/or in place;
   a control device for controlling the vibrating device which at least once actuates the vibrating device for a predetermined period of time before instrument information is detected or repeatedly detected; and
   a comparing device for comparing the first detection result and the second detection result,
   wherein the comparing device outputs a positive evaluation regarding the correctness of detected instruments if the first detection result matches the second detection result, and
   wherein, when the first detection result and the second detection result are not matching, the comparing device compares the first detection result and the second detection result to a predetermined data set and outputs a positive evaluation if:
   at least one of the first and second detection results matches the predetermined data set, or
   a combination of the first and second detection results matches the predetermined data set.

2. The device according to claim 1, further comprising a display device by which an evaluation and product-specific information are displayed, wherein the predetermined data set contains additional information which is output by the display device when an instrument is identified.

3. The device according to claim 1, further comprising a device for changing a relative orientation of the instruments and/or for changing a relative distance between the instruments and the first and second detecting devices.

4. The device according to claim 1, further comprising a tunnel reader, the tunnel reader comprising an encapsulated housing that forms a pass-through.

5. A method for simultaneously identifying a plurality of different surgical instruments or instrument groups, the method comprising the steps of:
   moving the plurality of different surgical instruments or instrument groups relative to a first detecting device and a second detecting device;
   detecting instruments with the first detecting device by a first detection technology as a first detection result, the first detection technology comprising an RFID technology;
   detecting instruments with the second detecting device by a second detection technology as a second detection result, the second detection technology comprising optical instrument shape identification;
   comparing the first detection result and the second detection result with a comparing device, wherein a positive evaluation is output if the first detection result matches the second detection result; and
   actuating a vibrating device for a predetermined period of time when no positive evaluation can be output, wherein after actuating the vibrating device, the first and second detection results are repeatedly detected,
   wherein, when the first detection result and the second detection result are not matching, the comparing device compares the first detection result and the second detection result to a predetermined data set and outputs a positive evaluation if:
   at least one of the first and second detection results matches the predetermined data set, or
   a combination of the first and second detection results matches the predetermined data set.

* * * * *